United States Patent [19]

Ohnuma et al.

[11] Patent Number: 4,912,204

[45] Date of Patent: Mar. 27, 1990

[54] FLUORO-SUBSTITUTED EPIPODOPHYLLOTOXIN GLUCOSIDES

[75] Inventors: Takeshi Ohnuma, Tokyo; Tetsuro Yamasaki, Yokahama; Hideo Kamei, Tokyo; Takayuki Naito, Kawasaki, all of Japan

[73] Assignee: Bristol-Myers Company, New York, N.Y.

[21] Appl. No.: 240,971

[22] Filed: Sep. 6, 1988

[51] Int. Cl.$^4$ ............................................. C07H 15/24
[52] U.S. Cl. .................................. 536/18.1; 536/4.1; 536/122
[58] Field of Search ..................... 536/18.1, 4.1, 122; 514/27

[56] References Cited

U.S. PATENT DOCUMENTS

| | | | |
|---|---|---|---|
| 3,524,844 | 8/1970 | Keller-Juslen et al. | 260/210 |
| 4,547,567 | 10/1985 | Umezawa et al. | 536/17.2 |
| 4,564,675 | 1/1986 | Kurabayashi et al. | 536/18.1 |
| 4,716,221 | 12/1987 | Umezawa et al. | 536/17.2 |
| 4,757,138 | 7/1988 | Fujii et al. | 536/18.1 |

*Primary Examiner*—John W. Rollins
*Assistant Examiner*—Elli Peselev
*Attorney, Agent, or Firm*—Mollie M. Yang

[57] ABSTRACT

The present invention provides antitumor fluoro-substituted 4'-demethylepipodophyllotoxin glucosides.

5 Claims, No Drawings

FLUORO-SUBSTITUTED EPIPODOPHYLLOTOXIN GLUCOSIDES

BACKGROUND OF THE INVENTION

1. Field of the Invention

The present invention relates to fluoro substituted 4'-demethylepipodophyllotoxin glucosides, to their use as antitumor agents, and to pharmaceutical compositions containing them.

2. Background Art

4'-Demethylepipodophyllotoxin glucosides of formula I are antitumor agents derived from the naturally occurring lignan, podophyllotoxin II. The method for their

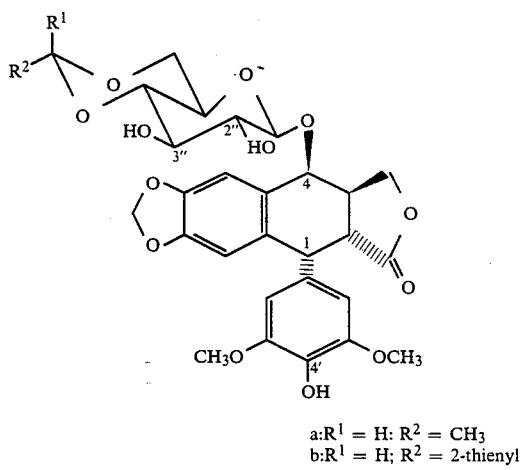

a: $R^1$ = H; $R^2$ = $CH_3$
b: $R^1$ = H; $R^2$ = 2-thienyl

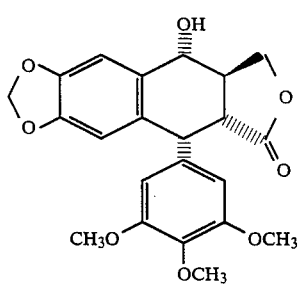

synthesis is described in U.S. Pat. No. 3,524,844 to Keller-Juslen et al. Among compounds of formula I, etoposide (Ia) and teniposide (Ib) have been established as clinically useful against a variety of tumors including small cell lung, ovarian, testicular, breast, bladder, brain, non-lymphocytic leukemia, and Hodgkin's disease.

U.S. Pat. Nos. 4,547,567 and 4,716,221 disclose compounds of formula III

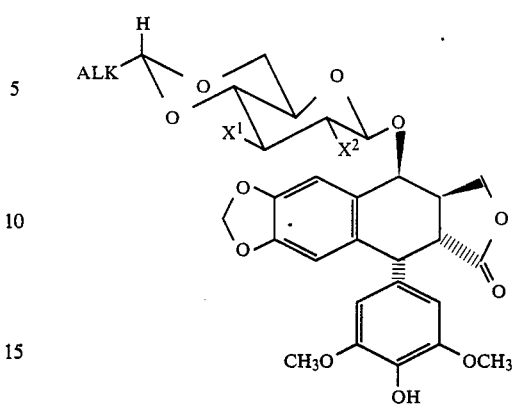

wherein one of $X^1$ and $X^2$ is OH, and the other is an amino, a monoalkylamino, or a dialkylamino group. These derivatives are said to exhibit high water solubility and they represent examples of epipodophyllotoxin glucosides in which the substituents on the sugar portion are modified.

SUMMARY OF THE INVENTION

The present invention provides antitumor compounds of formula IV

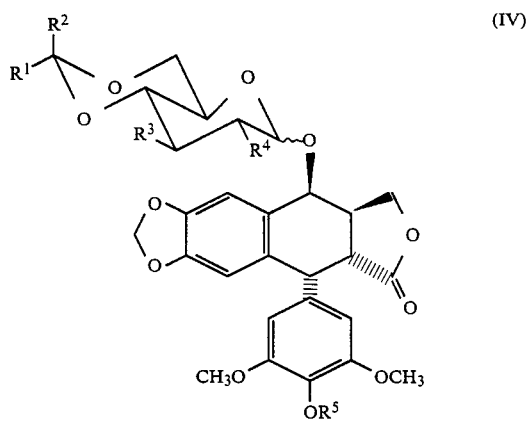

wherein $R^2$ is H and $R^1$ is selected from the group consisting of $(C_{1-10})$alkyl; $(C_{2-10})$alkenyl; $(C_{5-6})$cycloalkyl; 2-furyl; 2-thienyl; $(C_{6-10})$aryl; $(C_{7-14})$aralkyl; and $(C_{8-14})$aralkenyl wherein each of the aromatic rings may be unsubstituted or substituted with one or more groups selected from halo, $(C_{1-8})$alkyl, $(C_{1-8})$alkoxy, hydroxy, nitro, and amino; or $R^1$ and $R^2$ are each $(C_{1-8})$alkyl; or $R^1$ and $R^2$ and the carbon to which they are attached join to form a $(C_{5-6})$cycloalkyl group; one of $R^3$ or $R^4$ is OH and the other is F; $R^5$ is H or a phenol protecting group; and ⁓ represents an α- or β-glycosidic linkage.

DETAILED DESCRIPTION OF THE INVENTION

Compounds of the present invention having the general formula IV may be prepared by condensing 4'-protected-4'-demethylepipodophyllotoxin V

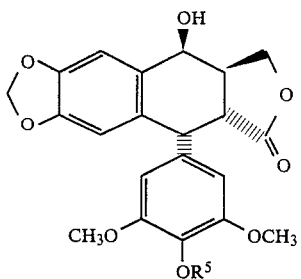

wherein $R^5$ is a phenol-protecting group, with a compound of formula VI

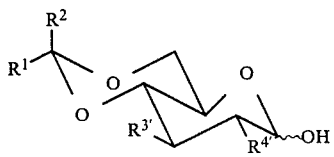

wherein $R^1$ and $R^2$ are as above defined, and one of $R^{3'}$ or $R^{4'}$ is a protected hydroxyl group and the other is F, to give a compound of formula VII

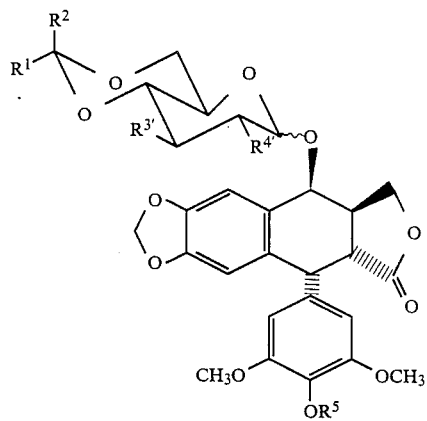

wherein $R^1$, $R^2$, $R^{3'}$, $R^{4'}$, $R^5$ and ∿ are as previously defined. The condensation reaction is carried out in an inert organic solvent, for example methylene chloride or ethylene chloride, at a temperature below 0° C., and in the presence of a catalyst such as boron trifluoride ethyl etherate. The reaction time may be from about 10 minutes to about 5 hours, preferably from about 30 minutes to about 1.5 hours. The action of boron trifluoride ethyl etherate may be quenched by the addition to the reaction mixture a tertiary amine such as pyridine or triethylamine. The choice of hydroxyl and phenol protecting groups is not particularly restricted and may include the formation of acyl derivatives such as esters and carbonates, ethers, acetals, and the like. These protecting groups may be removed using conventional deblocking methods, the choice of which depends on the nature of the protecting groups employed. Typical methods that may be mentioned include hydrogenation, acid or base catalyzed hydrolysis, and alcoholysis in the presence of a metal catalyst such as zinc powder or zinc acetate. It is not critical which of the hydroxy or phenol protecting group is removed first, or the protecting groups may be chosen such that they may be removed in the same step.

Compound of formula VI in turn may be prepared by reacting a sugar of formula VIII

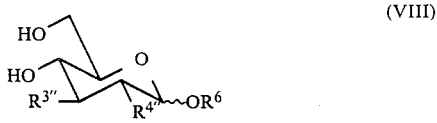

wherein one of $R^{3''}$ or $R^{4''}$ is hydroxy or protected hydroxyl and the other is F, and $R^6$ is H or a hydroxy protecting group; with a carbonyl compound of formula $R^1C(O)R^2$ or an acetal or a ketal thereof, wherein $R^1$ and $R^2$ are as above-defined. The reaction is carried out in an inert organic solvent such as methylene chloride, ethylene chloride, acetonitrile, tetrahydrofuran, or mixtures thereof, in the presence of an acid catalyst, for example hydrochloric acid, sulfuric acid, toluenesulfonic acid, or a Lewis acid such as zinc chloride. The reaction temperature may be from about 10° C. to about 50° C., and preferably at ambient temperature. The compound of formula VIII wherein one of $R^{3''}$ or $R^{4''}$ is hydroxy may be converted to the corresponding hydroxy-protected compound using conventional methods such as formation of ester, ether, or acetal; for compounds of formula VIII wherein $R^6$ is a hydroxyl protecting group, said hydroxyl protecting group may be selectively removed by treatment with, for example, alumina as described by Herzig and Nudelman, *Carbohydrate Research*, 1986, 153: 162–167.

The starting materials for compounds of formula VIII, viz. 2-deoxy-2-fluoro-D-glucose, 3-deoxy-3-fluoro-D-glucose, and their acylated derivatives may be prepared according to literature procedures; for example the procedure of Kovac, *Carbohydrate Research*, 1986, 153: 168–170 for the preparation of 2-deoxy-2-fluoro-D-glucose, and the procedure given in Tewson and Welch, *J. Org. Chem.*, 1978, 43: 1090–1092 for making 3-deoxy-3-fluoro-D-glucose.

Alternatively, the above described reaction sequence may be varied by first condensing V with a sugar of formula IX

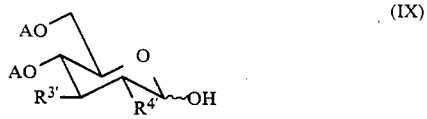

wherein $R^{3'}$ and $R^{4'}$ are as defined above, and A is a hydroxy protecting group, to form a compound of formula X

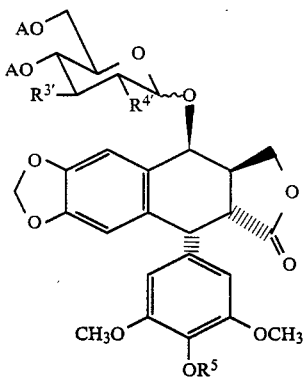

(X)

wherein A, $R^{3'}$, $R^{4'}$, and $R^5$ are as defined above. The removal of the hydroxyl protecting groups followed by coupling with $R^1C(O)R^2$ or an acetal or a ketal thereof provides compounds of formula IV.

It has been noted that the condensation of V with a fluoro-D-glucopyranose or a protected derivative thereof, or with its 4,6-O-acetal or ketal derivatives may result in a mixture of α- or β-glycosides. The mixture may be separated into the individual components using known separation techniques such as column chromatography. The separation of the isomers may be effected at any convenient time in the reaction sequence.

BIOLOGICAL ACTIVITY

Representative compounds of the present invention were evaluated for antitumor activity against murine transplantable P388 leukemia. Five-week old female $CDF_1$ mice were inoculated intraperitoneally with 0.4 ml of diluted ascitic fluid containing $10^6$ lymphocytic leukemia P388 cells. Test compounds were administered intraperitoneally as a single dose on day 1 and animals were observed for 45 days. The percent increase of median survival time (MST) of treated animals over that of untreated control animals was determined and reported as % T/C. Compounds showing % T/C values of 125 or greater are considered to have significant antitumor activity. Table I presents the results of the in vivo evaluation; only the maximum % T/C and the dose giving the maximum effects are reported.

TABLE I

| Antitumor activity against P388 leukemia | | |
|---|---|---|
| Compound | Dose (mg/kg/day) | % T/C of MST |
| Etoposide | 120 | 250 |
| XVI | 60 | 155 |
| XVII | 30 | 140 |
| XVIII | 30 | 185 |

Accordingly, the present invention provides a method for inhibiting mammalian tumors which comprises administering an effective tumor-inhibiting dose of an antitumor compound of formula IV to a tumor bearing host. For this purpose, the drug may be administered by conventional routes including, but not limited to, intravenous, intramuscular, intratumoral, intraarterial, intralymphatic, and oral.

A further aspect of the present invention provides a pharmaceutical composition which comprises a compound of formula IV and a pharmaceutically acceptable carrier. The antitumor composition may be made up of an pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are for illustrative purposes only and should not be construed as limiting the scope of the invention which is defined solely by the claims appended to this application.

Preparation of Starting Materials

A. Preparation of 3-O-acetyl-4,6-O-ethylidene-2-deoxy-2-fluoro-D-glycose (XI)

a. 2-Deoxy-2-fluoro-D-glucose (XII)

2-Deoxy-2-fluoro-D-glucose was prepared according to the method described by Kovac, P. (*Carbohydrate Research*, 1986, 153: 168–170). The first step of teh reaction involves the conversion of D-mannose into 1,3,4,6-tetra-O-acetyl-β-D-mannopyranose and is a modification of the procedure described by Deferrari, J. O. et al (*Carbohydrate Research*, 1967, 4: 432–434).

The acetic anhydride (50 ml) was added a few mg of D-mannose followed by 70% perchloric acid (2 drops). To the yellow solution was added D-mannose (13.2 g, 7.3 mmol) portionwise with continuous stirring during 35 minutes, the internal temperature being kept at 40°–45° C. The mixture was kept at room temperature for 60 minutes, and then cooled to 15° C., and phosphorus tribromide (10.6 ml) was added dropwise while the internal temperature was kept at 20°–25° C. Water (4.6 ml) was added and the mixture was kept for 60 minutes at room temperature. A solution of sodium acetate trihydrate (40 g) in water (50 ml) was slowly added, the internal temperature being kept at 35°–40° C., and the resulting yellow solution was kept at this temperature for 10 minutes. The solution was then poured into ice-water, and the mixture was extracted with chloroform (3×40 ml). The chloroform extracts were combined and successively washed with cold water, cold sodium bicarbonate solution, and cold water, and dried over anhydrous magnesium sulfate. The organic solution was evaporated to dryness and the residue was crystallized from ether to yield 5.3 g (21%) of 1,3,4,6-tetra-O-acetyl-β-D-mannopyranose as colorless crystals. MP 163°–165° C. (lit. 164°–165° C.).

To a solution of 1,3,4,6-tetra-O-acetyl-β-D-mannopyranose (4.9 g, 14 mmol) in dry dioxane (35 ml) was added diethylamine sulfur trifluoride (5.1 ml, 42 mmol). The mixture was stirred at 100°–105° C. (bath) for 10 minutes, cooled to 0° C., and methanol (2 ml) was added. The mixture was poured into aq. sodium bicarbonate solution (80 ml) and extracted with methylene chloride (3×30 ml). The extract were dried over sodium bicarbonate. The organic phase was evaporated to dryness, and the residue was purified on a silica gel column (MeOH:CH$_2$Cl$_2$=1:10) to give colorless oil, which was crystallized form ether-isopropyl ether yielding 2.56 g (52%) of 1,3,4,6-tetra-O-acetyl-2-deoxy-2-fluoro-β-D-glucopyranose, colorless crystals, MP 94°–96° C. (lit. 95°–96° C.).

A solution of the tetraacetate (2.43 g, 6.9 mmol) in methanol (20 ml) was treated with 28% methanolic sodium methoxide (6.0 ml, ca. 30 mmol) and kept at room temperature for three hours. After neutralization with conc. sulfuric acid at 0° C., the inorganic precipitate was filtered off and the filtrate was concentrated in vacuo. The residue was further evaporated to dryness with benzene to give 1.30 g of XII, which was submitted, without purification, to the following ethylidenation reaction.

b. 1,3-Di-O-acetyl-2-deoxy-4,6-O-ethylidene-2-fluoro-D-glucopyranose (XIII)

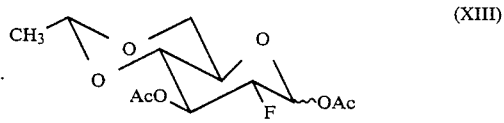

(XIII)

To a suspension of 2-deoxy-2-fluoro-D-glucose (XII, 1.26 g, 6.9 mmol) in methylene chloride (60 ml) and tetrahydrofuran (10 ml) was added acetaldehyde (2.0 ml) and concentrated sulfuric acid (two drops). The mixture was stirred at room temperature for 15 hours, washed with aqueous sodium bicarbonate, and then dried over sodium sulfate. The organic solvent was evaporated in vacuo to give 480 mg (34%) of 2-deoxy-4,6-O-ethylidene-2-fluoro-D-glucopyranose as an oil showing a single spot on silica gel TLC (R$_f$ 0.61, CH$_2$Cl$_2$:MeOH=5:1). This oil was acetylated without further purification. Acetic anhydride (1.0 ml) was added to a solution of the above-obtained oil (150 mg, 0.72 mmol) in pyridine (2.0 ml) and the mixture was stirred at room temperature overnight. Methanol (1.0 ml) was added to the mixture and stirring continued for an additional hour. The mixture was concentrated in vacuo and the residue was diluted with ethyl acetate (30 ml). The solution was washed successively with 5% hydrochloric acid, aqueous sodium bicarbonate, and water; dried over anhydrous sodium sulfate, and the solvent evaporated to give 150 mg (71%) of XIII as an oil comprising a 1:1 mixture of anomers.

IR $\nu_{max}$ (Neat) cm$^{-1}$ 1730. $^1$H NMR (CDCl$_3$) δ 6.33 (0.5H, d, J=4 Hz, 1-β-H), 5.79 (0.5H, dd, J=4 and 8 Hz, 1-α-H), 4.63 (1H, q, J=5 Hz, 7-H), 2.20 and 2.16 (6H, each s, COCH$_3$), 1.33 (3H, d, J=5 Hz, 7-CH$_3$).

c. 3-O-Acetyl-2-deoxy-4,6-O-ethylidene-2-fluoro-D-glucopyranose (XI)

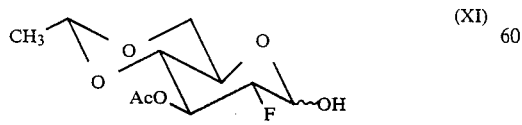

(XI)

A suspension of XIII (150 mg, 0.51 mmol) and alumina (3 g, Woelm I) in methanol (15 ml) was heated at 60° C. for four hours with vigorous stirring. The inorganic material was filtered off and the filtrate was concentrated in vacuo to give 117 mg (91%) of XIV as a colorless oil.

$^1$H NMR (60 MHz, CDCl$_3$) δ 5.3 (0.5H, m, 1-β-H), 4.89 (0.5H, m, 1-α-H), 4.63 (1H, q, J=5 Hz, 7-H), 2.12 (3H, s, COCH$_3$), 1.30 (3H, d, J=5 Hz).

B. Preparation of 2,4,6-tri-O-acetyl-3-deoxy-3-fluoro-D-glucopyranose (XIV)

a. 1,2,4,6-Tetra-O-acetyl-3-deoxy-3-fluoro-D-glucopyranose (XV)

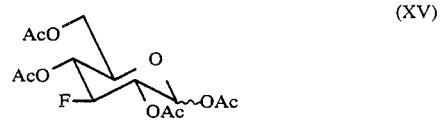

(XV)

1,2,4,6-Tetra-O-acetyl-3-deoxy-3-fluoro-D-glucopyranose was prepared according to the procedure described by Tewson and Welch (J. Org. Chem., 1978, 43: 1090–1092).

To a solution of 1,2:5,6-bis-O-isopropylidene-α-D-allofuranose (7.00 g, 27 mmol), [which was prepared in three steps from D-glucose according to the Baker's method (Carbohydr. Res., 1972, 24: 192–197)], and N,N-dimethylaminopyridine (6.1 g, 50 mmol) in methylene chloride (50 ml) was slowly added diethylaminosulfur trifluoride (5.4 ml, 41 mmol) under argon at −10° C. The reaction mixture was stirred at room temperature overnight, methanol (5 ml) was slowly added and the resulting solution was diluted with methylene chloride (50 ml). The solution was washed with saturated sodium bicarbonate and dried (Na$_2$SO$_4$). The organic phase was evaporated in vacuo to give a crude brown oil, which was purified on a silica gel column chromatography (hexane:AcOEt=9:1) to give 3.77 g (53%) of 3-deoxy-3-fluoro-1,2:5,6-bis-O-isopropylidene-α-D-glucofuranose as colorless oil.

A suspension of the 3-fluoro-di-O-isopropylidene glucose (2.62 g, 10 mmol) and Amberlite IR-120(H+) cation-exchange resin (4.5 g) in water (45 ml) was heated at 50° C. with vigorous stirring for four hours. The resin was filtered off and the filtrate was concentrated in vacuo to give an oil, which, without purification was submitted for the following acetylation. To a solution of the oil in acetic anhydride (20 ml) was added 70% perchloric acid (2 drops) at room temperature. After being stirred for one hour, the reaction mixture was cooled to 0° C. and methanol (10 ml) was added. The mixture diluted with methylene chloride (50 ml) was washed with aq. sodium bicarbonate and water, and dried (Na$_2$SO$_4$). The organic phase was evaporated to give 1.58 g (45%) of XV as a colorless oil, which was crystallized from petroleum ether to afford colorless crystals, MP 115°–121° C. (lit. 116°–120° C.).

b. 2,4,6-Tri-O-acetyl-3-deoxy-3-fluoro-D-glucopyranose (XIV)

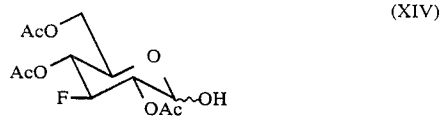

(XIV)

To a solution of XV (1.60 g, 4.5 mmol) in methylene chloride (8 ml) was added 25% hydrogen bromide in acetic acid (8 ml). The mixture was stirred at room temperature overnight, diluted with methylene chloride (50 ml), washed successively with water, aqueous sodium bicarbonate, and water, and dried over anhydrous sodium sulfate. The organic solvent was evaporated in vacuo to give a brown oil (1.58 g). To a solution of this crude oil in 20% aqueous acetone (40 ml) was added mercuric cyanide (1.26 g, 5.0 mmol). The mixture was stirred at room temperature for three hours, concentrated in vacuo, diluted with ethyl acetate (50 ml), washed with water, 1N sodium bromide, and then dried over anhydrous sodium sulfate. The organic solvent was evaporated to yield XIV as colorless crystals (1.07 g, 77%).

MP 115°–120° C. IR $\nu_{max}$ (Nujol) cm$^{-1}$ 3530, 1755, 1735. $^1$H NMR (60 MHz, CDCl$_3$-DMSO-d$_6$) δ 5.33 (1H, m, 4-H), 5.00 (1H, d, J=8 Hz, 1-H), 4.83 (1H, m, 2-H), 4.5 (1H, m, 3-H), 4.16 (2H, m, 6-H), 3.67 (1H, m, 5-H).

EXAMPLE 1

Synthesis of 2″-deoxy-2″-fluoroetoposide (XVI) and its 1″-α-anomer (XVII).

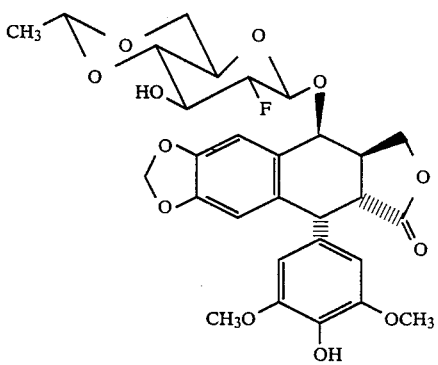

(XVI)

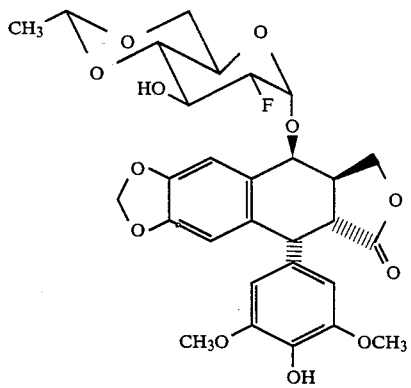

(XVII)

To a cooled (−15° to −20° C.) solution of 4′-benzyloxycarbonyl-4′-demethylepipodophyllotoxin methanol solvate (200 mg, 0.35 mmol; dried at 110° in vacuo prior to use) and 3-O-acetyl-4,6-O-ethylidene-2-deoxy-2-fluoro-D-glucose (110 mg, 0.44 mmol) in ethylene dichloride (20 ml) was added boron trifluoride ethyl etherate (125 μl, 1 mmol) under argon atmosphere. After the reaction mixture had been stirred at −15° C. for 50 minutes, triethylamine (0.2 ml) was added thereto and the resulting solution was washed with water, and then dried over anhydrous sodium sulfate. The organic solvent was evaporated in vacuo and the resulting crude residue (320 mg) in acetone (5 ml) and ethanol (30 ml) was hydrogenated with 10% palladium on carbon (150 mg) at 1 atm. The catalyst was filtered off and the filtrate was concentrated in vacuo to give 170 mg of a crude mixture of 3″-O-acetyl-2″-deoxy-2″-fluoroetoposide and its α-anomer.

A suspension of the crude mixture of phenols (170 mg) and zinc acetate dihydrate (240 mg) in methanol (40 ml) was refluxed for 30 hours. The organic solvent was evaporated in vacuo to give 124 mg of an amorphous solid which showed two major spots on TLC (R$_f$ 0.47 and 0.40; 2% MeOH/CH$_2$Cl$_2$). The two components were separated by silica gel column chromatography (2% MeOH/CH$_2$Cl$_2$) to give 50 mg of XVI (19% overall yield; R$_f$ 0.47) and 20 mg of XVII (8% overall yield; R$_f$ 0.40) as colorless crystals from ethanol.

XVI: MP 207°–209° C. Estimated purity: 95% by HPLC (LiChrosorb RP-18, 70% MeOH-H$_2$O). IR $\nu_{max}$ (Nujol) cm$^{-1}$ 3300, 1765, 1615. $^1$H NMR (400 MHz, CDCl$_3$-DMSO-d$_6$) δ 4.82 (1H, dd, J=3.7 and 7.7 Hz, 1″-H), 4.74 (1H, q, J=4.8 Hz, 7″-H), 4.18 (1H, dd, J=4.4 and 9.9 Hz, 6″-Heq), 4.14 (1H, dt, J=7.7 and 50.6 Hz, 2″-H), 3.83 (1H, m, 3″-H), 3.56 (1H, t, J=9.9 Hz, 6″-Hax), 3.3 (2H, m, 4″, 5″-H), 1.37 (3H, d, J=4.8 Hz, 8″-H).

XVII: MP 163°–168° C. Estimated purity: 70% by HPLC. IR $\nu_{max}$ (Nujol) cm$^{-1}$ 3350, 1760, 1615. $^1$H NMR (400 MHz, CDCl$_3$) δ 4.73 (1H, d, J=2.9 Hz, 1″-H), 4.68 (1H, q, J=4.8 Hz, 7″-H), 4.4 (1H, m, 2″-H), 4.10 (1H, dd, J=4, 10.6 Hz, 6″-Heq), 3.83 (1H, m, 3″-H), 3.50 (1H, t, J=10.6 Hz, 6″-Hax), 3.3 (2H, m, 4″, 5″-H), 1.34 (3H, d, J=4.8 Hz, 8″-H).

EXAMPLE 2

Synthesis of 3″-deoxy-3″-fluoroetoposide (XVIII)

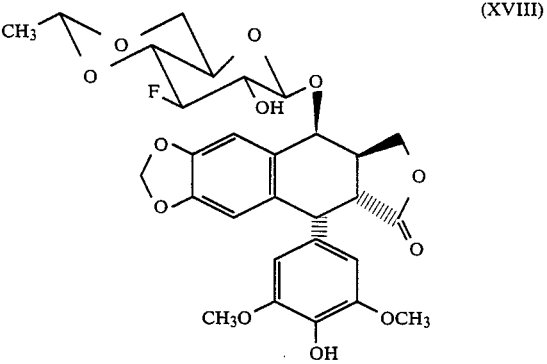

(XVIII)

To a cooled (−15° C.) solution of XIV (462 mg, 1.5 mmol) and 4′-benzyloxycarbonyl-4′-demethylepipodophyllotoxin (534 mg, 1 mmol) in ethylene dichloride (30 ml) was added boron trifluoride ethyl etherate (380 μl, 3 mmol) under argon. The solution was stirred at −15° C. for 1 hour and then pyridine (0.3 ml) was added thereto. The resulting solution was washed with water, 5% hydrochloric acid and aqueous sodium bicarbonate, and dried over anhydrous sodium sulfate. The organic solvent was evaporated in vacuo to give 1.19 g of a crude amorphous solid, which was purified by silica gel column (2% MeOH-CH$_2$Cl$_2$) to give 659 mg (89%) of 4-O-(2,4,6-tri-O-acetyl-3-deoxy-3-fluoro-β-D-glucopyranosyl)-4′-benzyloxycarbonyl-4′-demethylepipodophyllotoxin (XIX)

A suspension of XIX (412 mg, 0.5 mmol) and zinc acetate dihydrate (1.24 g, 5.7 mmol) in methanol (30 ml) was refluxed for 20 hours. The mixture was concentrated in vacuo and the resulting residue in CH$_2$Cl$_2$ (70 ml)-AcOH (0.5 ml) was washed with water and aqueous sodium bicarbonate and dried over anhydrous sodium sulfate. The organic solvent was evaporated in vacuo to give 370 mg of 4-O-(3-deoxy-3-fluoro-β-D-glucopyranosyl)-4'-demethylepipodophyllotoxin (XX) as an amorphous solid, which without purification was ethylidenated as follows.

To a suspension of the amorphous solid (370 mg) in methylene chloride (70 ml) was added acetaldehyde dimethyl acetal (0.2 ml) and concentrated sulfuric acid (one drop). After stirring at room temperature for five hours, the mixture was washed with aqueous sodium bicarbonate and dried over anhydrous sodium sulfate. The organic solvent was evaporated in vacuo to give 160 mg of amorphous solid, which was purified by silica gel column (2% MeOH-CH$_2$Cl$_2$) to give 87 mg (29%) of 3''-deoxy-3''-fluoroetoposide (XVIII) as colorless crystals from methanol.

MP 285°–287° C. Estimated purity 95% by HPLC. $^1$H NMR (400 MHz, CDCl$_3$) δ 4.76 (1H, q, J=5.1 Hz, 7''-H), 4.66 (1H, d, J=7.7 Hz, 1''-H), 4.54 (1H, dt, J=8.4 and 53.5 Hz, 3''-H), 4.2 (1H, m, 6''-Heq), 3.68 (1H, dt, J=2.6 and 8.4 Hz, 2''-H), 3.60 (1H, t, J=10.3 Hz, 6''-Hax), 3.54 (1H, t, J=9.3 Hz, 4''-H), 3.32 (1H, m, 5''-H), 2.40 (1H, d, J=2.6 Hz, 2''-OH).

We claim:
1. A compound having the formula

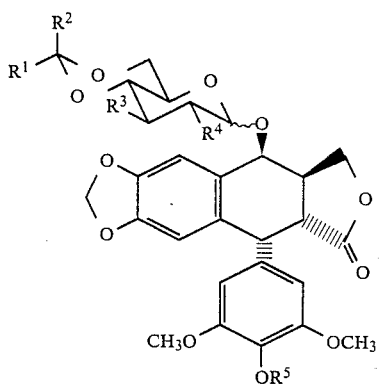

wherein
R$^2$ is H and R$^1$ is selected from the group consisting of (C$_{1-10}$)alkyl; (C$_{2-10}$)alkenyl; (C$_{5-6}$)cycloalkyl; 2-furyl; 2-thienyl; (C$_{6-10}$)aryl; (C$_{7-14}$)aralkyl; and (C$_{8-14}$)aralkenyl wherein each of the aromatic rings may be unsubstituted or substituted with one or more groups selected from halo, (C$_{1-8}$)alkyl, (C$_{1-8}$)alkoxy, hydroxy, nitro, and amino; or R$^1$ and R$^2$ are each (C$_{1-8}$)alkyl; or R$^1$ and R$^2$ and the carbon to which they are attached join to form a (C$_{5-6}$)cycloalkyl group;

one of R$^3$ or R$^4$ is OH and the other is F;
R$^5$ is H or a phenol protecting group; and
∼∼ represents an α- or β-glycosidic linkage.

2. A compound of claim 1 wherein R$^2$ and R$^5$ are each H, and R$^1$ is selected from methyl, 2-thienyl and phenyl.

3. A compound having the formula

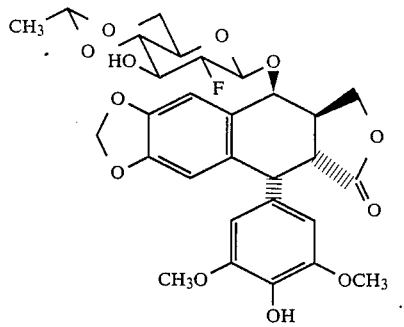

4. A compound having the formula

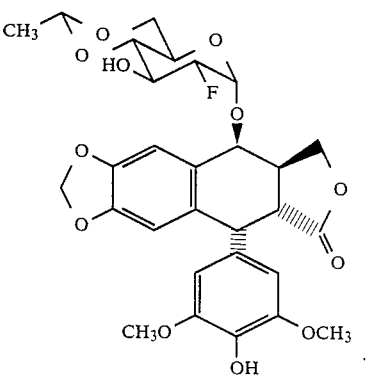

5. A compound having the formula

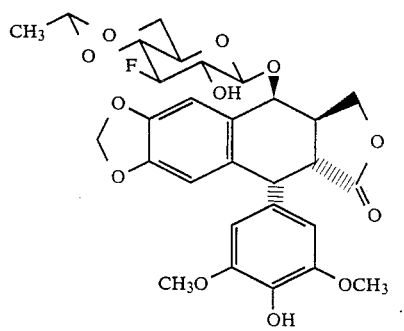

* * * * *